US012253518B2

(12) United States Patent
Ger et al.

(10) Patent No.: US 12,253,518 B2
(45) Date of Patent: Mar. 18, 2025

(54) MAGNETIC CONTROL SYSTEM BASE ON MEASUREMENT OF TARGET MOLECULE ADSORPTION

(71) Applicant: Chung Yuan Christian University, Taoyuan (TW)

(72) Inventors: Tzong-Rong Ger, Taoyuan (TW); Hong-Siang Wang, Taoyuan (TW); Yu-Che Cheng, Taoyuan (TW); Hsing-Cheng Chu, Taoyuan (TW); Jing-Wen Tsai, Taoyuan (TW); Chia-Ke Tsou, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 567 days.

(21) Appl. No.: 17/497,870

(22) Filed: Oct. 8, 2021

(65) Prior Publication Data

US 2022/0113303 A1    Apr. 14, 2022

(30) Foreign Application Priority Data

Oct. 8, 2020    (TW) ................................ 109135014

(51) Int. Cl.
*G01N 33/543* (2006.01)
*G01N 21/17* (2006.01)
*G01N 21/82* (2006.01)

(52) U.S. Cl.
CPC ... *G01N 33/54333* (2013.01); *G01N 21/1717* (2013.01); *G01N 21/82* (2013.01);
(Continued)

(58) Field of Classification Search
CPC ......... G01N 33/54333; G01N 21/1717; G01N 21/82; G01N 33/54326; G01N 33/54346; G01N 2021/1727
See application file for complete search history.

(56) References Cited

U.S. PATENT DOCUMENTS 9,841,421 B2 * 12/2017 Dittmer ................. G01N 27/72
9,863,863 B2 *  1/2018 Schleipen ........ G01N 33/54326
(Continued)

FOREIGN PATENT DOCUMENTS

TW        201819913 A      6/2018

OTHER PUBLICATIONS

Beckman-Coulter, Inc., "Coulter TQ-Prep Workstation Instructions for Use", Jun. 2010, PN 4237396BA, (Pages in order of appearance in Action: 1-1, 2-4, 5-4, 2-9, 1-8, 1-2, 2-2, and 3-1,) (Year: 2010).*

*Primary Examiner* — Edmond C Lau
*Assistant Examiner* — Joshua M Carlson
(74) *Attorney, Agent, or Firm* — Chun-Ming Shih; LANWAY IPR SERVICES

(57) ABSTRACT

The present invention provides a magnetic-control measurement system, comprises a reaction container and a programable magnetron measurement unit. The reaction container is configured to fill a target suspension having a plurality of magnetic nanoparticles (MNPs); the programable magnetron measurement unit comprises: an opaque housing, a loading platform is configured to place the reaction container, a light-emitting device is configured to generate a high directional light through the reaction container, a magnetic field generator is disposed on opposite two sides of the loading platform for generating an alternating magnetic field forced on the reaction container in an operating time, a sensing device is configured to detect a light intensity variance of the high directional light through the reaction container, a processor is configured to calculate a value and an efficiency of absorption of the target suspension, and a display is communicatively coupled to the processor, to display the value and the efficiency of absorption of the target suspension.

16 Claims, 8 Drawing Sheets

(52) U.S. Cl.
CPC . *G01N 33/54326* (2013.01); *G01N 33/54346* (2013.01); *G01N 2021/1727* (2013.01)

(56) References Cited

U.S. PATENT DOCUMENTS

| | | | |
|---|---|---|---|
| 10,161,856 B1* | 12/2018 | Wu | G01N 35/0098 |
| 2012/0003750 A1* | 1/2012 | Ranzoni | G01N 21/51 |
| | | | 422/69 |
| 2012/0046203 A1* | 2/2012 | Walsh | G01N 35/0098 |
| | | | 422/69 |
| 2013/0105581 A1* | 5/2013 | Kwon | G06K 19/022 |
| | | | 235/493 |
| 2014/0120632 A1* | 5/2014 | Ranzoni | G01N 27/745 |
| | | | 436/501 |
| 2017/0145487 A1* | 5/2017 | Nagaoka | G01N 33/54333 |
| 2021/0270827 A1* | 9/2021 | Preira | G01N 33/54388 |
| 2022/0184634 A1* | 6/2022 | Schreier | B03C 1/0332 |

\* cited by examiner

MAGNETIC CONTROL SYSTEM BASE ON MEASUREMENT OF TARGET MOLECULE ADSORPTION

This application claims the benefit of Taiwan Patent Application Serial No. 109135014, filed Oct. 8, 2020, the subject matter of which is incorporated herein by reference.

BACKGROUND OF INVENTION

1. Field of the Invention

The present invention is related to a technique for separation and adsorption of a magnetic molecule, and more particularly, to a portable magnetic control system for immediate determining and display the value and efficiency of absorption of the magnetic molecule.

2. Description of the Prior Art

In the field of medical diagnosis, sensor devices based on verification are rapidly gaining popularity because they can accurately determine the presence and concentration of many analytes of interest in various samples, such as saliva, blood, serum, plasma, urine, and other body fluid samples. Target molecules are a popular field of research in recent times and have a wide range of applications, including biotechnology, food science, and drug development. However, before conducting target molecule research, sample pre-treatment is an extremely important step to obtain specific target molecules by some purification and isolation techniques, among which particle adsorption is the topic of most current studies.

Therefore, in recent years, the use of nano-particle analysis has been explored in different biosensing schemes. The commonly used sensing methods include nano-particle analysis, in which nano-magnetic beads are attached to the biomolecules to be tested and an applied magnetic field is applied in a specific area. or concentration of the object to be measured. The remote interaction between the magnetic particles and an external magnetic field allows for easy manipulation and sensitive detection. The main advantages offered by biosensing methods using magnetic fields and magnetic carriers are that the biomedia has a low magnetization rate and the magnetic interaction is largely independent of surface charge, pH, ion concentration or temperature. In addition, the realization of a magnetic carrier-based method to capture, classify and detect target analytes in biological media is particularly attractive due to the potential low cost, simplicity of the device and the high sensitivity that can be achieved.

Magnetic particles have superparamagnetic properties, high saturation magnetization strength, low cytotoxicity, and good biocompatibility, which are widely used in the biological and medical fields. However, the magnetic sensing element must be able to sense the change of magnetic field of the beads in order to estimate the density of molecules adhering to the beads. Since the magnetic field is applied to the beads by magnetic force generators, it is important to avoid the magnetic field generated by these magnetic force generators from affecting the magnetic sensing element since the magnetic sensing element will also respond to the applied magnetic field generated by the magnetic force generators.

SUMMARY OF THE INVENTION

The present invention provides a portable magnetic-control measurement system in which the system is formed by special structural configuration and circuit design of magnetic components, step motors, display screen, control interface, and other components so that the distance of magnetic components, frequency, intensity, and time of magnetic field are controlled to be changed. In addition, the data of efficiency and amount of adsorption of the target molecule (e.g. magnetic nanoparticles) to be measured are obtained through specific algorithms and displayed on the display screen for users to understand the measurement results visually. Further, the overall magnetic-control measurement system is small and portable for users to make real-time measurements and analyses regardless of geographical or environmental restrictions.

In one embodiment, the present invention provides the portable magnetic-control measurement system comprise a reaction container and a programable magnetron measurement unit. The reaction container is configured to fill a target suspension having a plurality of magnetic nanoparticles (MNPs); the programable magnetron measurement unit comprises an opaque housing, a loading platform, a light-emitting device, a magnetic field generator, a sensing device, a processor, and a display. The loading platform is configured to place the reaction container, the light-emitting device is configured to generate a high directional light through the reaction container, the magnetic field generator is disposed on opposite two sides of the loading platform to generate an alternating magnetic field forced on the reaction container in an operating time, the sensing device is configured to detect a light intensity variance of the high directional light through the reaction container in the operating time, the processor is communicatively coupled to the loading platform, the light-emitting device, the magnetic field generator, and the sensing device, to calculate a value and an efficiency of absorption of the target suspension and the display is communicatively coupled to the processor, to display the value and the efficiency of absorption of the target suspension.

In one embodiment, the operating time further comprises a starting time and an ending time, an initial data of light intensity at the starting time and a final data of light intensity at the ending time are formed by the sensing device respectively while the high directional light through the reaction container, and the value and the efficiency of absorption of the target suspension are calculated respectively through the initial data of light intensity and the final data of light intensity by the processor.

In one embodiment, the target suspension is mainly a mixed solution, which is a biological molecular solution doped with a plurality of the magnetic nanoparticles (MNPs), and the biological molecular solution being selected from proteins, cells, strains, antibodies, or drugs mixed with a solvent.

In one embodiment, the programable magnetron measurement unit further comprises a control interface disposed on the upper cover for adjusting a plurality of operating parameters, which at least include a strength of alternating magnetic field and a frequency of alternating magnetic field.

In one embodiment, the magnetic field generator comprises a control circuit and a couple of electromagnet devices having an excitation coil, and the electromagnet devices are movably disposed on opposite two sides of the loading platform along a first direction respectively, and the control circuit is communicatively coupled to the processor and the electromagnet devices, to receive a voltage signal from the processor and to control the current flowing through the excitation coil for changing the strength of alternating magnetic field.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
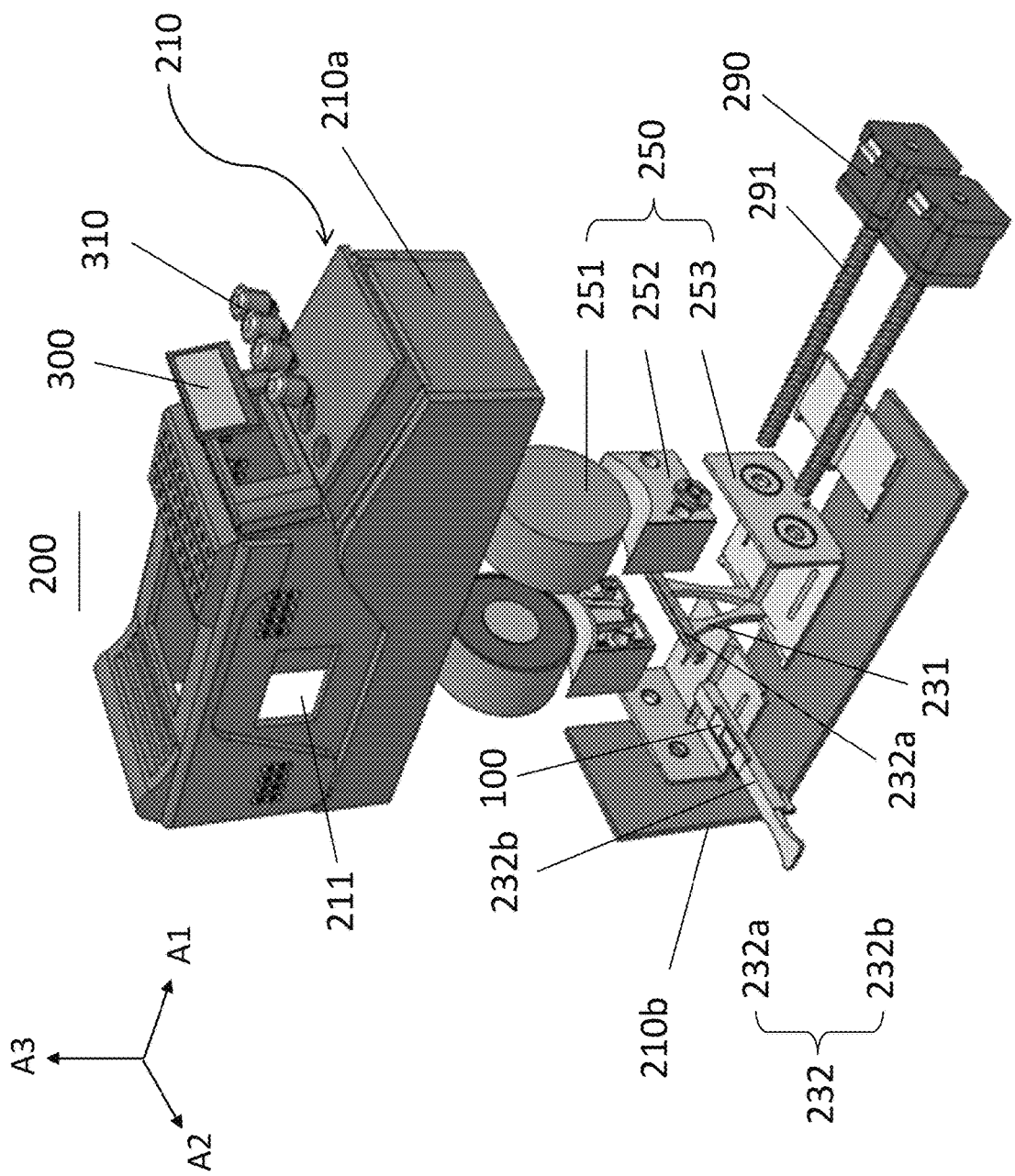
FIG. 1 illustrates a diagram of the appearance decomposition of the portable magnetic-control measurement system, in accordance with aspects of the present specification.

The invention disclosed herein is directed to a portable magnetic-control measurement system of target molecule adsorption. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

In order to have a clearer understanding of the technical features, purpose and effect of the present invention, the specific manner of implementation of the present invention is described in detail with respect to the attached drawings. However, the attached drawings are for reference and illustration purposes only and are not intended to limit the present invention; the foregoing and other technical contents, features and effects of the present invention will be clearly presented in the following detailed descriptions of each embodiment with reference to the drawings. The directional terms mentioned in the following examples, such as "up", "down", "left", "right", "front", "back", etc., are merely references to the directions shown in the additional illustrations. Therefore, the directional terms used are for illustrative purposes and are not intended to limit the present creation; furthermore, in each of the following embodiments, the same or similar components will be used with the same or similar component designations.

Before describing the present invention, the main motive of the invention and the purpose and efficacy of developing the magnetic-control measurement system disclosed by the invention based on this motive are mentioned. 2004, Z. G. Peng and other scholars proposed to study the effect of bovine serum albumin (BSA) on the adsorption behavior of magnetic particles under different pH environments and found that the maximum adsorption occurred with or without carbodiamine. The adsorption behavior decreases as the pH increases or decreases. The adsorption behavior decreases faster when the pH is less than 4.7, and conversely, the adsorption behavior decreases slower when the pH is greater than 4.7 because of the greater intermolecular repulsion and conformational changes that occur in the acidic range.

In 2006, N. Shamim et al. suggested that the isoelectric point of polymer-coated magnetic particles is 6.2, while the isoelectric point of bare magnetic particles is 6.74. Through different pH values, it can be found that the adsorption of BSA can be explained by the electrostatic interaction force between BSA and magnetic particles. In the same way, when the pH is lower (pH=5.23), the BSA is negatively charged and the magnetic particles are positively charged, and the electrostatic attraction between them should cause them to attract each other. Nevertheless, it was found that the conformational change of the target molecules was not affected when the environmental pH was around the isoelectric point, and the structure was compact, so that a larger adsorption amount could be produced.

Based on the above-mentioned arguments and the shortcomings of conventional knowledge, the present invention proposes a magnetically controlled measurement system based on the adsorption of target molecules.

Figure 2:
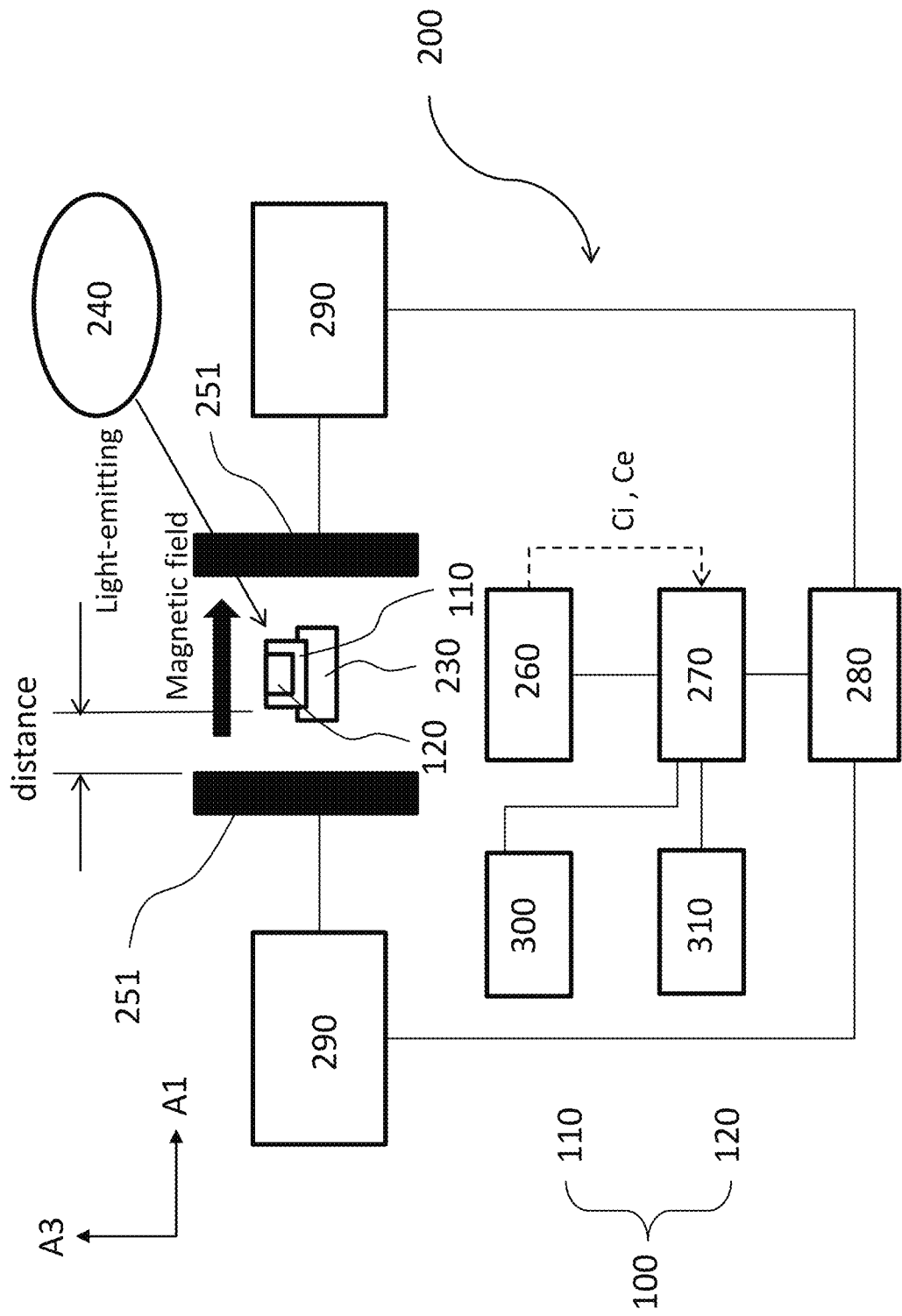
FIG. 2 illustrates a block diagram of the portable magnetic-control measurement system of FIG. 1.

Please refer to FIGS. 1 and 2, wherein FIG. 1 illustrates a diagram of the appearance decomposition of the portable magnetic-control measurement system according to one embodiment of the present invention, and FIG. 2 illustrates a block diagram of the portable magnetic-control measurement system of FIG. 1. The portable magnetic-control measurement system comprises a sample 100 and a programable magnetron measurement unit 200; wherein the sample 100 includes a reaction container 110, configured to fill a target suspension 120 having a plurality of magnetic nanoparticles (MNPs).

In the present embodiment, the target suspension 120 contains a target molecule, and the "target molecule" may be any molecule whose concentration or presence is to be determined, e.g., the target molecule is a strain, cell, protein, antibody, drug, or chemical molecule. Examples of target molecules are molecular targets such as proteins, enzymes, endocrines, peptides, nucleic acids, and cellular targets such as pathogenic cells, bacterial cells, and fungal cells. The subject molecule itself may be present in one of the analyzed samples or may be formed in the sensor device in situ (e.g., by a reaction occurring in a sensor device (not shown). If the sensor device is used to monitor a reaction, the subject may be the starting product of the reaction or a reaction product. References to "in solution" below mean that the reaction or assay is performed in a liquid environment. The participating reagents need not be dissolved in a fluid medium; but may be present in suspension or dispersion.

Based on the above-mentioned, the above reaction container 110 can be defined as an analytical sample cavity in which a sample fluid in solution having one of the components to be detected (e.g., drugs, antibodies, DNA, etc.) can be provided. Moreover, the reaction container 110 is a cassette-type box which is made of glass or plastic, and the reaction container 110 has a chamber for filling with the target suspension 120, and the reaction container 110 further has a light-penetration area and the light-penetration area is about at least 60% of the overall of the reaction container, it means to be fully or partially transparent. Further, the target suspension 120 is synthesized by using co-precipitation in which the biological molecular solution and the magnetic nanoparticles (MNPs) are pre-mixed and fill the target suspension 120 into the reaction container 110.

In the present embodiment, the cassette as a whole may be a thin flat piece of a one-sided (rectangular) configuration, but without limitation. The reaction container 110 can also imagine alternatives, such as different forms of microfluidic devices. These include microcapillary valves, micro-needles for injecting, diluting, and mixing samples to be analyzed, and one of the analogous microfluidic devices. The magnetic particle suspension, which is a mixture of magnetic particles and biological samples, may be prepared in advance or may be mixed in the reaction zone through a system provided with two diversion channels (not shown) connected to the reaction container 110, one to guide the magnetic particles and the other to guide the biological samples and diverted to the reaction container 110 respectively.

In addition, the magnetic nanoparticles of the target suspension 120, such as super smooth magnetic beads. Substantially spherical particles, in the sense that each individual magnetic particle has negligible optical anisotropy. Alternative shapes may be used, such as (for example) elliptical or ovoid particles (irregular shape). Magnetic particles can also be magnetic beads, such as magnetic polymeric beads. Magnetic particle suspensions may contain more than one type of particle mixed together. Different types of particles may have different sizes or different properties, such as magnetic or non-magnetic (as long as one of these particle types is magnetic). The size of the individual particle types can vary from the particle level to the micron level. If there is a target molecule, the use of larger particles can stop the rotation of smaller particles. The number of magnetic particles may be one or more, depending on the number, concentration, or density of biological molecules, and is not limited to the present invention.

As mentioned above, in order to efficiently capture very small amounts of biomolecules floating in solution, it is necessary to increase the collision frequency between the biomolecules and the molecules on the capture side. Therefore, we investigated the use of tiny magnetic particles of less than 1 μm as a method for capturing molecules. By using these tiny magnetic nanoparticles, the surface area per unit number of particles can be increased, and the molecular motion can be enhanced, thus improving the efficiency of the reaction with biomolecules.

According to the above, the smaller the particle size of the magnetic particles In the present embodiment, the higher the capture efficiency and the higher the number of particles that can be fixed on a certain area, and therefore the higher the density, which is more favorable for high sensitivity detection and high-speed detection. Therefore, in the specific embodiment, the structure of the reaction container 110 is designed to hold the solution containing tiny magnetic particles on a highly wetted plate, and the thickness of the chamber filled with the target suspension 120 is designed to be as thin as possible in all directions to provide a magnetic field to attract magnetic particles from both sides of a flat substrate.

In the present embodiment, the programable magnetron measurement unit 200 mainly comprises an opaque housing 210, a loading platform 230, a light-emitting device 240, a magnetic field generator 250, a sensing device 260, a processor 270, a programmable logic controller 280, a step motor 290 and a display 300; wherein the programable magnetron measurement unit 200 is powered by an external power supply for the operation of each of the above components, e.g., utility power.

The opaque housing 210 is consists of an upper cover 210a and a lower base 210b, and the upper cover 210a is detachably assembled to the lower base 210b to define a receiving space which all around is opaque, to receive the loading platform 230, the light-emitting device 240, the magnetic field generator 250, the sensing device, and the display 260 is disposed on the upper cover 210a for observing. Basically, the upper cover 210a and the lower base 210b is formed to the overall external dimensions of the programable magnetron measurement unit 200, and the overall height is not more than 40 cm, the overall width is not more than 30 cm, and the overall length is not more than 60 cm. The design of the device is mainly based on the concept of space-saving and is easy to carry. The carrier 230 is connected to the base 220 and configured in the space, in principle, in the central position of the device, but not limited to the present invention.

In the present embodiment, the loading platform 230 further includes a fixing frame 231 and a slide rail kit 232 connected with the fixing frame 231. The slide rail kit 232 comprises a supporting rail 232a and a loading body 232b, and the loading body 232b having a groove portion on its surface of one side for inserting the reaction container 100, and the loading body 232b having a slideway portion on its surface of another side, which is being slidably and separably connected to the supporting rail 232a along a second direction A2.

In the present embodiment, the upper cover 210a further includes a gate door 211 disposed near to the loading platform 230, and the gate door 211 is openable and closable, and the loading body 232b can be taken into inside of the opaque housing 100 and connected to the supporting rail 232a along the second direction A2 while the gate door 211 is open. It is mainly used to facilitate the user to place the above-mentioned sample 100 to be measured 100 on the loading platform 230 through the gate door 211 for subsequent measurement operations, and the size of the gate door 211 is not limited.

The light-emitting device 240 is configured to generate a high directional light through the reaction container 100, may be a beam emitting, for example, a laser, a UV lamp, an IR lamp, a halogen lamp, or the like, in the ultraviolet (UV), visible, or infrared (IR) spectral range. The emitted beam is usually linearly polarized as it leaves the light source. In addition, there is no limitation on the color of the light field generated by light source 240, it can be white light, color light, or choose the appropriate light according to the target, for example, if the target can produce fluorescence, then the light-emitting device 240 that can stimulate the target to produce fluorescence can be used to implement.

The magnetic field generator 250 is disposed on opposite two sides of the loading platform 230, to generate an alternating magnetic field forced on the reaction container 110 in an operating time. Basically, the magnetic field generator 250 comprises a control circuit, a couple of electromagnet devices 251 having an excitation coil, a couple of support bases 252, and a couple of linkage bases 253. The electromagnet devices 251 are provided with the support base 252 on the bottom side to support the electromagnet devices 251, and the support bases 252 are fixed on the linkage bases 253, and the support bases 252 are connected to the above-mentioned step motor 290; wherein the operating time further comprises a starting time (T1) and an ending time (T2).

As mentioned above, the electromagnet devices 251 are movably disposed on opposite two sides of the loading platform 230 along a first direction A1 respectively, and the control circuit is communicatively coupled to the processor 270 and the electromagnet devices, to receive a voltage signal from the processor 270 and to control the current flowing through the excitation coil for changing the strength of alternating magnetic field.

Moreover, the magnetic field generator 250 is externally powered to generate the alternating magnetic field for generating a plurality of magnetic lines of force with a frequency range (fr) and a magnetic field strength range (Gr) to be applied to the target suspension 120 at the start time (T1) to the end time (T2). By using the perturbation of the magnetic field to increase the magnetic field perturbation is used to increase the target molecular adsorption benefit of the magnetic particles. The magnetic field generator 250 is generated to a magnetic field that oscillates at a variable frequency between a start frequency and an end frequency, and the magnetic field generator 250 changes the direction of the applied magnetic field by a control signal and repeatedly changes the direction of the applied magnetic field during the measurement process, thereby causing the magnetic particles in the magnetic nanoparticles to move back and forth.

The sensing device 260 is configured to detect a light intensity variance of the high directional light through the reaction container in the operating time, and the processor 270 is communicatively coupled to the loading platform 230, the light-emitting device 240, the magnetic field generator 250, and the sensing device 260, which is calculated to a value and an efficiency of absorption of the target suspension. Basically, an initial data (Ci) of light intensity at the starting time (T1) and a final data (Ce) of light intensity at the ending time (T2) are formed by the sensing device 260 respectively while the high directional light through the reaction container 110, and the value and the efficiency of absorption of the target suspension 120 are calculated respectively through the initial data of light intensity and the final data of light intensity by the processor.

In specific embodiments, sensing device 260 comprises two parts: real-time magnetic field sensing and real-time light sensing, the real-time magnetic field sensing part can be performed by "Hall probe", and the real-time light sensing can be performed by a photometric sensor containing a photoelectric crystal or a photoelectric diode, and the sensed analog signal is returned to the processor 270 for computing.

In specific embodiments, the processor 270 may be a microcontroller containing a CPU or MCU. The aforementioned signal generation and transmission to the processor 270 and the control of the information processing of adjustable operating parameters are known techniques and will not be further described here.

In the present inventor, the efficiency of absorption of the target suspension is calculated according to the formula as below:

$$\text{efficiency of absorption } (P1) = \frac{Ci - Ce}{Ci - B}$$

parameter Ci is the initial data of light intensity;
parameter Ce is the final data of light intensity;
parameter B is the reference data of background.

According to the above, the value of absorption of the target suspension is calculated according to the formula as below:

$$\text{value of absorption } (P2) = \frac{V \times M \times P1}{W}$$

parameter V is a volume of the biological molecular solution;
parameter M is a concentration of the biological molecular solution before reacting;
parameter W is a weight of the magnetic nanoparticles (MNPs) being doped;
parameter P1 is the efficiency of absorption of the target suspension.

As described above, the volume of the target suspension 120 (ml), the concentration of the target suspension (mg/ml), and the reference weight of the magnetic molecule (g) can be measured during the preparation. Therefore, the value and efficiency of adsorption obtained can be calculated to generate the target molecule adsorption amount, and the numerical result of the target molecule adsorption amount can be displayed by the display 300 configured on the outer periphery of the opaque housing 210. The target molecule adsorption efficiency and the target molecule adsorption amount are displayed by the display element 300 configured on the outer periphery of the opaque housing 210. In specific embodiments, the display element may be an Organic Light-Emitting Diode (OLED).

In the present embodiment, the step motor 290 further a ball screw 291; wherein the linkage bases are connected to the ball screw, and the electromagnet devices 251 are detachably assembled to the linkage bases 253, and the programmable logic controller 280 is communicatively coupled to the processor 270 and the step motor 290, to receive a voltage signal from the processor 270 and to control the step motor 290 for driving the ball screw, to change the distance between the reaction container 110 and the electromagnet devices 251 in the first direction A1; wherein the first direction A1 and the second direction A2 are non-parallel.

In the present embodiment, the programable magnetron measurement unit 200 further comprises a control interface 310 disposed on the upper cover 210a for adjusting a plurality of operating parameters; wherein the operating parameters at least include a strength of alternating magnetic field, a frequency of alternating magnetic field, a light intensity of the light-detecting device, and a distance between the reaction container and the magnetic field generator. Further, the control interface 310 can be a button, knob, paddle, or other analog signal generating device, or a touch panel digital signal generating device. Although this illustration indicates a button-type device, it is not intended to be a limitation.

In the present embodiment, the operating parameters further include a plurality of conditions of the operating time, which at least comprises a duration of the operation time, a number of operation cycle, an interval time of operation cycle.

In the present embodiment, the operating parameters further include an operating condition of each operation in the operation cycle, which at least comprises the strength of alternating magnetic field, the frequency of alternating magnetic field, the light intensity of the light-detecting device, and the distance between the reaction container and the magnetic field generator.

It is noted that the hardware components of the magnetic-control measurement system described in this invention are clearly described in the above disclosure, and the part about controlling the operation of these hardware components, in the specific implementation, by using "Arduino" microprocessor to write itinerary; but not limited to the present invention.

Figure 3:
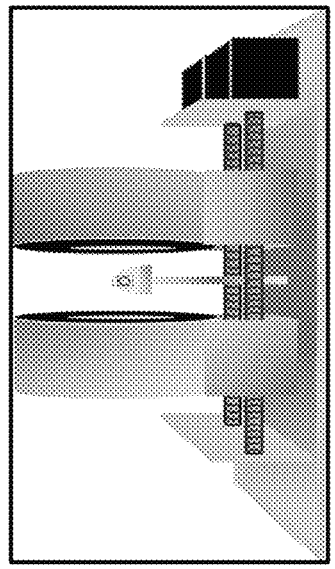
FIG. 3 illustrates a schematic representation of appearance structure of the portable magnetic-control measurement system of FIG. 1 according to one embodiment of the present invention.
Figure 3:
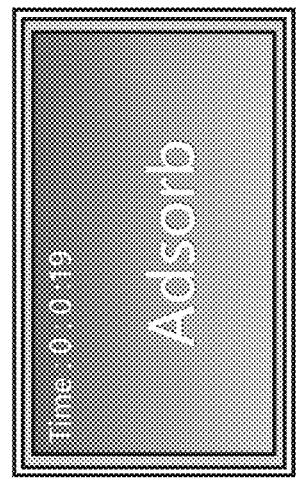
Figure 3:
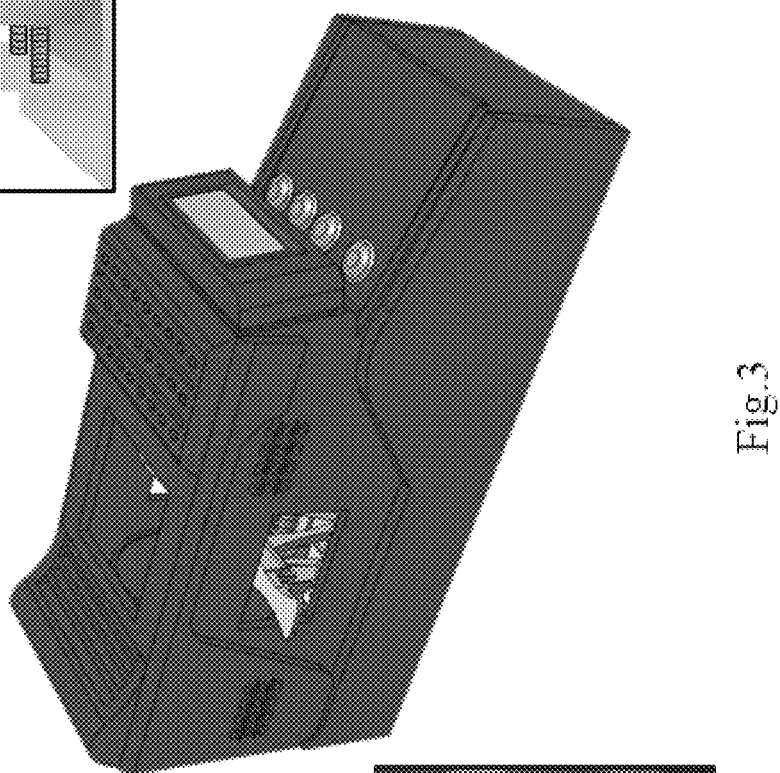
Figure 3:
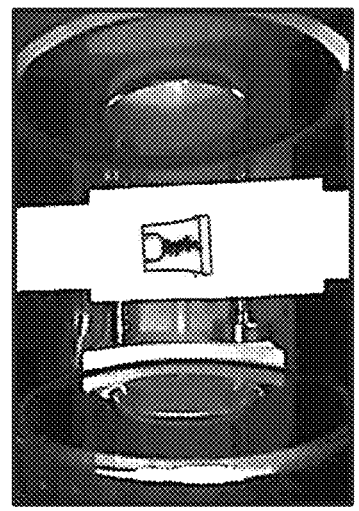

Please refer to FIG. 3, wherein FIG. 3 illustrates a schematic representation of appearance structure of the portable magnetic-control measurement system of FIG. 1 according to one embodiment of the present invention. According to the above system of the present invention will use magnetic nanoparticles without surface modification and bovine serum albumin (BSA solution) to investigate the adsorption effect. In addition, the magnetic field size, magnetic field frequency, and adsorption time were programmed and controlled to investigate the adsorption efficiency of proteins under different parameters.

Figure 4:
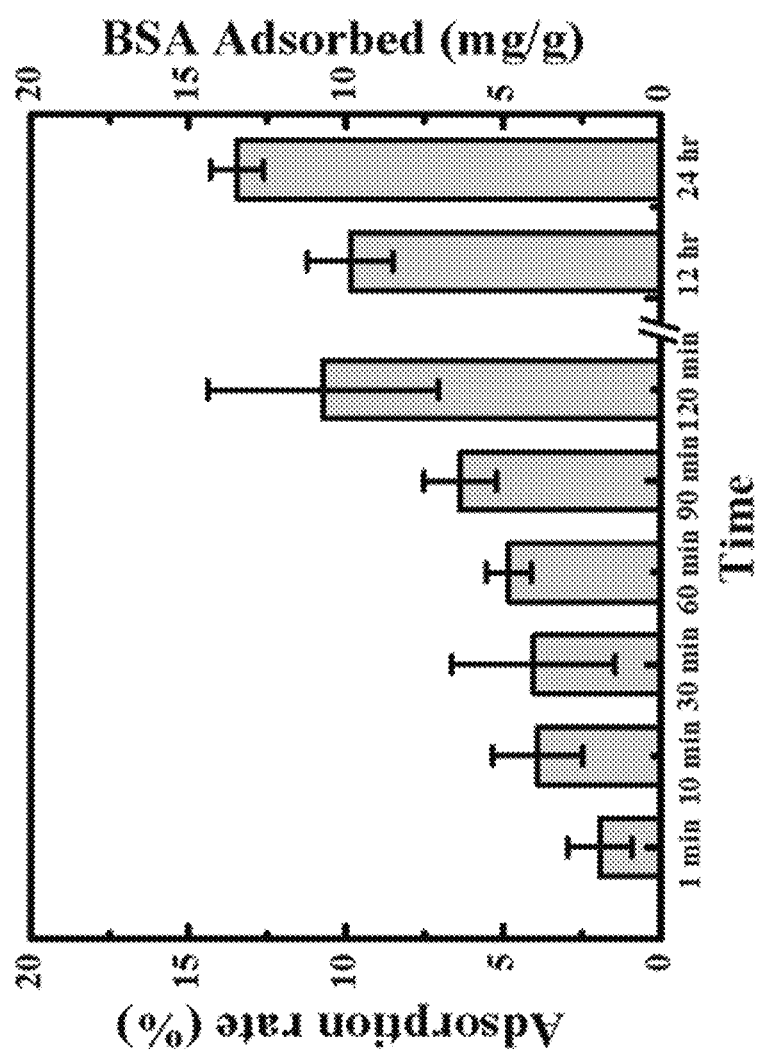
FIG. 4 illustrates a graphical representation of the variation of value and efficiency of absorption in using the portable magnetic-control measurement system of FIG. 1 without an alternating magnetic field forced on the reaction container.
Figure 5:
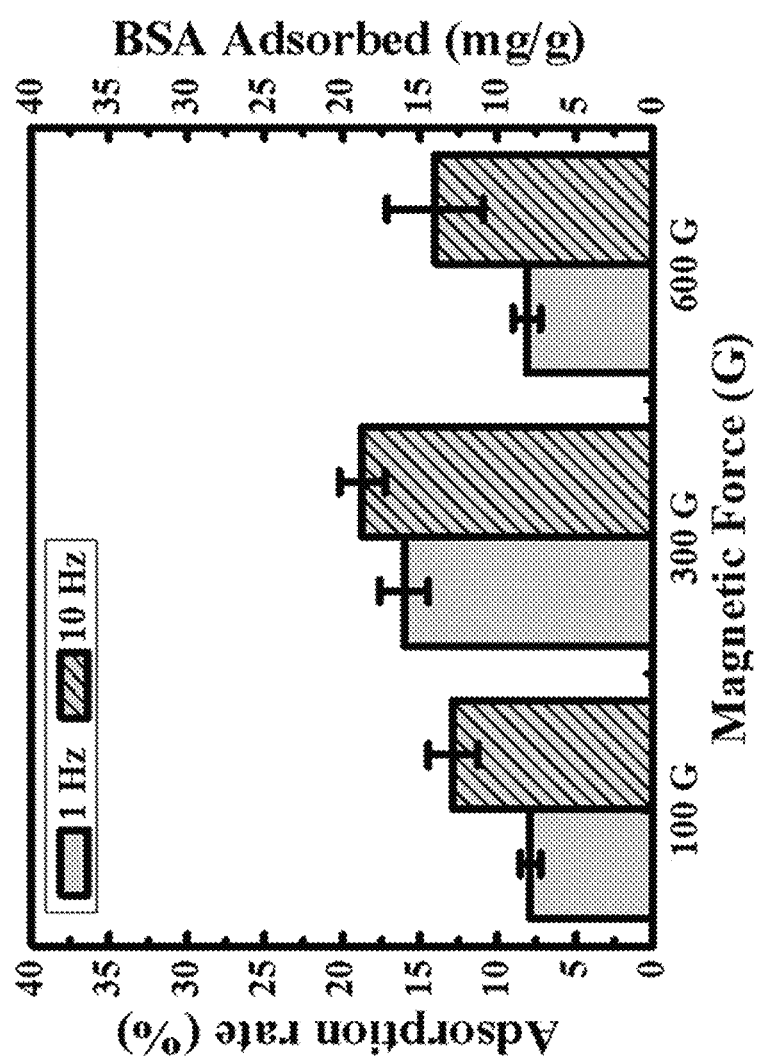
FIG. 5 illustrates a graphical representation of the variation of value and efficiency of absorption in using the portable magnetic-control measurement system of FIG. 1 with the different frequencies of an alternating magnetic field forced on the reaction container.
Figure 6A:
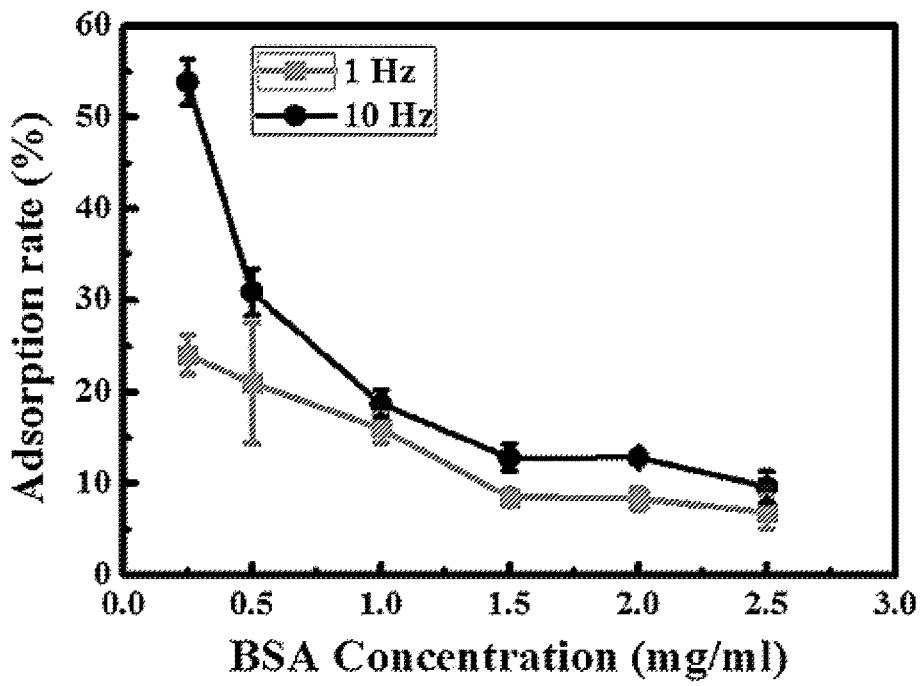
FIGS. 6a and 6b illustrate a graphical representation of the variation of value and efficiency of absorption in using the portable magnetic-control measurement system of FIG. 1 with the different frequencies of an alternating magnetic field forced on the reaction container.
Figure 6B:
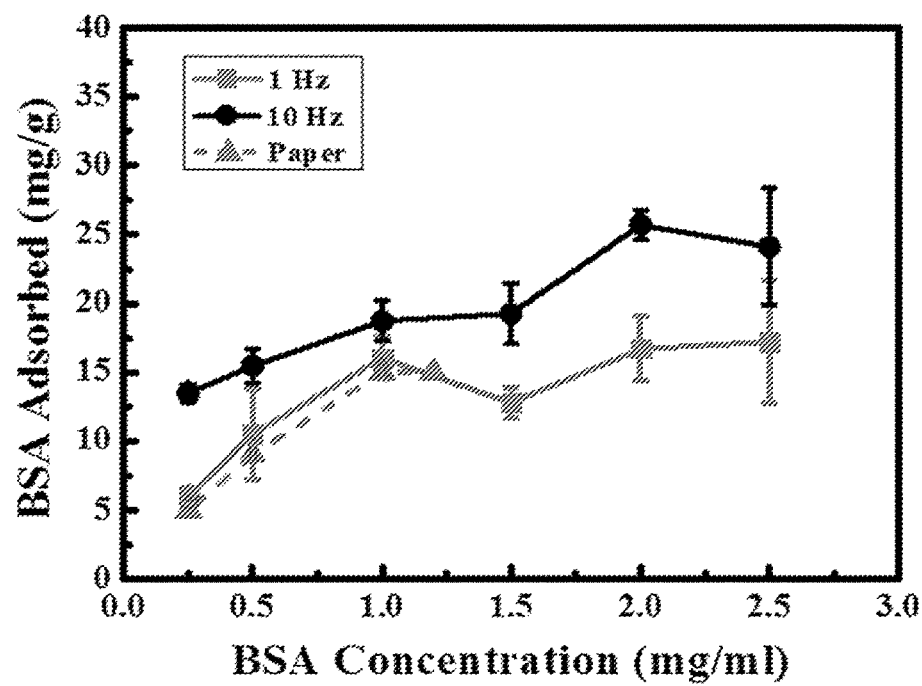
Figure 7A:
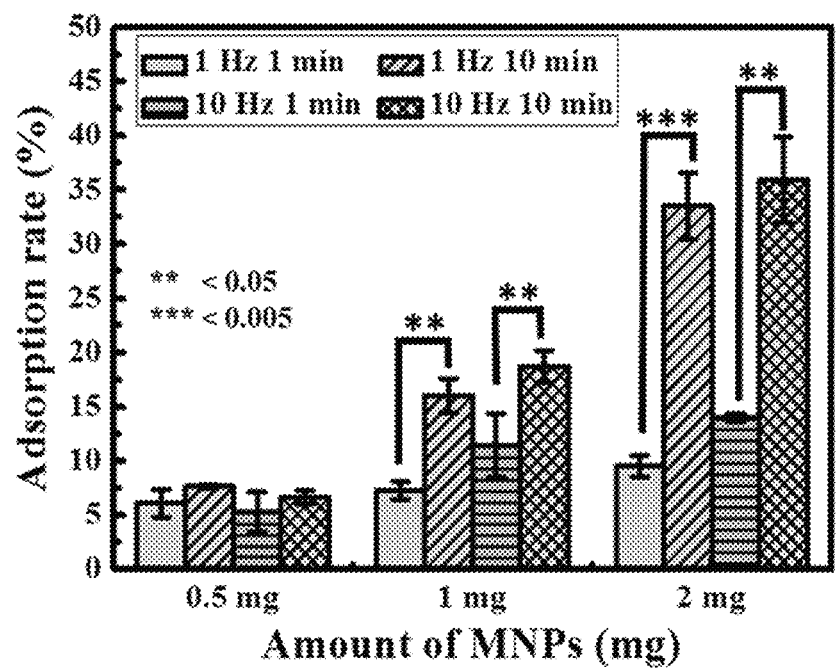
FIGS. 7a and 7b illustrate a graphical representation of the variation of value and efficiency of absorption in using the portable magnetic-control measurement system of FIG. 1 with the different amounts of magnetic nanoparticles (MNPs) in the reaction container.
Figure 7B:
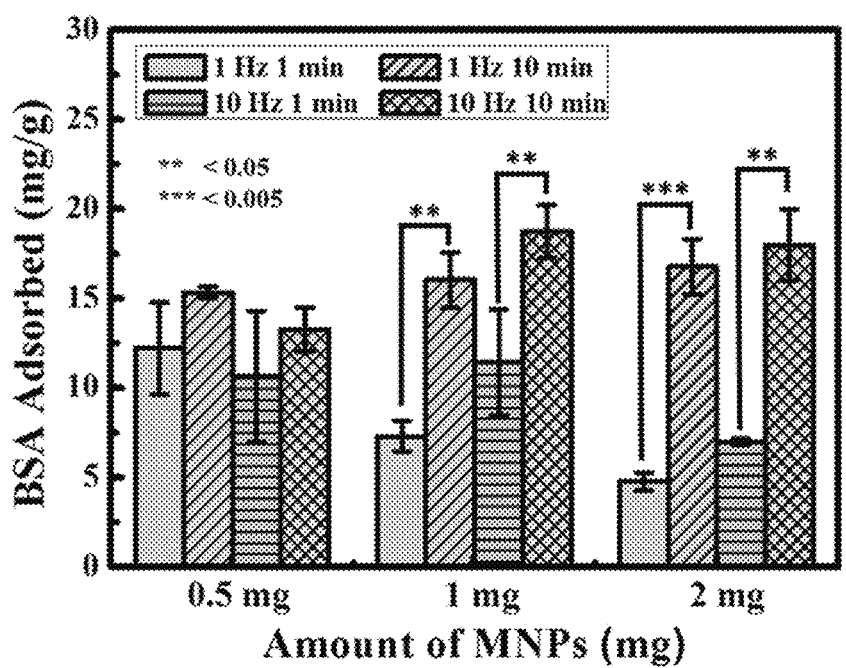
Figure 8:
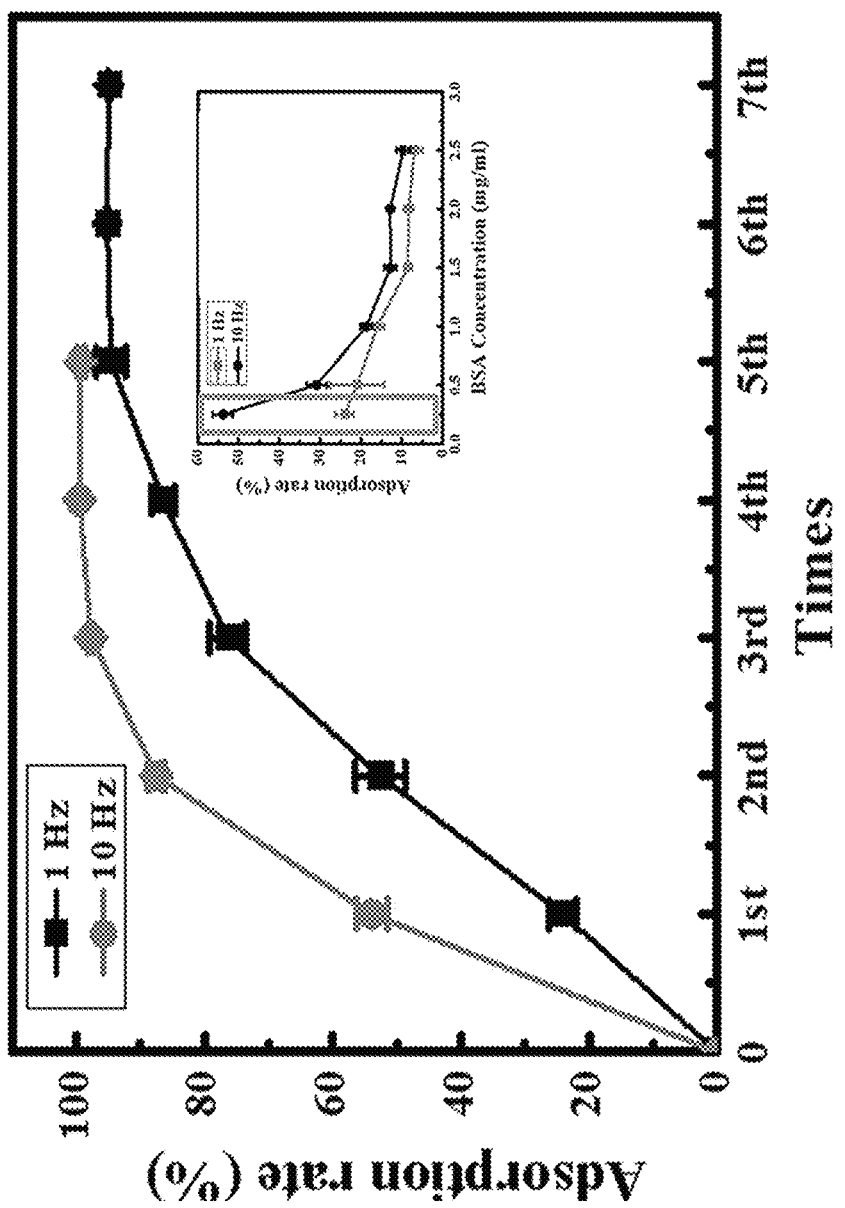
FIG. 8 illustrates a graphical representation of reliability verification results of repeated-absorption test in using the portable magnetic-control measurement system of FIG. 1.

Please refer to FIGS. 4, 5, 6a, 6b, 7a, 7b, and 8; wherein FIG. 4 illustrates a graphical representation of the variation of value and efficiency of absorption in using the portable magnetic-control measurement system of FIG. 1 without an alternating magnetic field forced on the reaction container. FIG. 5 illustrates a graphical representation of the variation of value and efficiency of absorption in using the portable magnetic-control measurement system of FIG. 1 with the different frequencies of an alternating magnetic field forced on the reaction container. FIGS. 6a and 6b illustrate a graphical representation of the variation of value and efficiency of absorption in using the portable magnetic-control measurement system of FIG. 1 with the different frequencies of an alternating magnetic field forced on the reaction container. FIGS. 7a and 7b illustrate a graphical representation of the variation of value and efficiency of absorption in using the portable magnetic-control measurement system of FIG. 1 with the different amounts of magnetic nanoparticles (MNPs) in the reaction container. FIG. 8 illustrates a graphical representation of reliability verification results of the repeated-absorption test in using the portable magnetic-control measurement system of FIG. 1.

The result is shown in FIG. 4, the magnetic nanoparticles (MNPs) without any magnetic field disturbance were deposited in the reaction container 110 and could not be uniformly mixed with the BSA solution, thus resulting in poor absorption, even though the adsorption rate was only below 15% by 24 hours.

The result is shown in FIG. 5, the magnetic field of 300 G has the highest adsorption capacity and adsorption rate. In terms of adsorption motion pattern, 300 G magnetic nanoparticles (MNPs) move completely with the magnetic field; 100 G magnetic nanoparticles (MNPs) shake in place; 600 G magnetic nanoparticles (MNPs) move only partially with the magnetic field, so we believe that the motion pattern of magnetic nanoparticles (MNPs) directly affects the adsorption effect.

The results are shown in FIGS. 6a and 6b, the trend shows that the adsorption effect of the magnetic nanoparticles (MNPs) is better at 10 Hz than at 1 Hz, indicating that the faster perturbation speed effectively increases the adsorption effect.

The results are shown in FIGS. 7a and 7b, the lower amounts of magnetic nanoparticles (MNPs), time, and magnetic field frequency did not produce significant differences in adsorption results, but as the amount of the magnetic nanoparticles (MNPs) increased, the differences became more pronounced, especially the difference in time, with 10 minutes of target molecule adsorption better than 1 minute of target molecule adsorption.

The result is shown in FIG. 8, the BSA concentration of 0.25 mg/ml was used for the experiment, and each time the adsorption was repeated for 10 minutes at a frequency of 10 Hz. The adsorption efficiency was close to 97% at the third repetition and close to 100% at the fourth repetition, thus proving that the system has the ability to separate trace target molecules.

This invention is mainly provided to the method for controlling the magnetic field to make the surface of magnetic nanoparticles with different chemical bonding (e.g., $NH3+$ or $COOH-$) to generate, in order to make magnetic nanoparticles and biological samples with different adsorption efficiency; or make the surface of magnetic nanoparticles with special structure, such as: increasing the roughness, or mesh structure can be used to adsorb specific biological samples. For example, the biological samples may be a mixture of two or more samples, and the magnetic nanoparticles with surface characteristics can be used to adsorb specific biological samples to achieve the effect of separating biological samples. Moreover, we were able to achieve nearly 100% adsorption efficiency by repeated adsorption, for trace molecules using magnetic nanoparticles in a short period of time, confirming the high reliability of the system with the ability to purify and isolate trace target molecules.

In summary, the present invention provides a portable magnetic-control measurement system in which the system is formed by special structural configuration and circuit design of magnetic components, step motors, display screen, control interface, and other components so that the distance of magnetic components, frequency, intensity, and time of magnetic field are controlled to be changed. In addition, the data of efficiency and amount of adsorption of the target molecule (e.g. magnetic nanoparticles) to be measured are obtained through specific algorithms and displayed on the display screen for users to understand the measurement results visually. Further, the overall magnetic-control measurement system is small and portable for users to make real-time measurements and analyses regardless of geographical or environmental restrictions. The small size of the system makes it easy to carry around for immediate measurement and analysis, regardless of geographical or environmental constraints.

While the present invention has been particularly shown and described with reference to a preferred embodiment, it will be understood by those skilled in the art that various changes in form and detail may be without departing from the spirit and scope of the present invention.

What is claimed is:

1. A portable magnetic-control measurement system, comprising:
    a reaction container configured to fill a target suspension having a plurality of magnetic nanoparticles (MNPs);
    a programable magnetron measurement unit comprises:
        an opaque housing;
        a loading platform configured to place the reaction container;
        a light-emitting device configured to generate a directional light through the reaction container;
        a magnetic field generator disposed on opposite two sides of the loading platform, to generate an alternating magnetic field forced on the reaction container in an operating time, wherein the magnetic field generator includes a linkage base and an electromagnet device, and the electromagnet device is detachably assembled to the linkage base;

a sensing device configured to detect a light intensity variance of the directional light through the reaction container in the operating time;

a processor communicatively coupled to the loading platform, the light-emitting device, the magnetic field generator and the sensing device, to calculate a value and an efficiency of absorption of the target suspension;

a display communicatively coupled to the processor, to display the value and the efficiency of absorption of the target suspension; and a programmable logic controller and a step motor, a ball screw connected to the linkage base, wherein the programmable logic controller is communicatively coupled to the processor and the step motor, to receive a voltage signal from the processor and to control the step motor to drive the ball screw for changing a distance between the reaction container and the electromagnet device in a first direction.

2. The system of claim 1, wherein the operating time further comprises a starting time and an ending time, an initial data of light intensity at the starting time and a final data of light intensity at the ending time are formed by the sensing device respectively while the directional light through the reaction container, and the value and the efficiency of absorption of the target suspension are calculated respectively through the initial data of light intensity and the final data of light intensity by the processor.

3. The system of claim 2, wherein the efficiency of absorption of the target suspension is calculated according to the formula as below:

$$\text{efficiency of absorption } (P1) = \frac{Ci - Ce}{Ci - B}$$

parameter Ci is the initial data of light intensity, parameter Ce is the final data of light intensity, parameter B is the reference data of background.

4. The system of claim 1, wherein the target suspension is mainly a mixed solution, which is a biological molecular solution doped with a plurality of the magnetic nanoparticles (MNPs), and the biological molecular solution being selected from proteins, cells, strains, antibodies or drugs mixed with a solvent.

5. The device of claim 4, wherein the value of absorption of the target suspension is calculated according to the formula as below:

$$\text{value of absorption } (P2) = \frac{V \times M \times P1}{W}$$

parameter V is a volume of the biological molecular solution, parameter M is a concentration of the biological molecular solution before reacting, parameter W is a weight of the magnetic nanoparticles (MNPs) being doped, parameter P1 is the efficiency of absorption of the target suspension.

6. The device of claim 4, wherein the target suspension is synthesized by using co-precipitation in which the biological molecular solution and the magnetic nanoparticles (MNPs) are pre-mixed, and fill the target suspension into the reaction container.

7. The device of claim 1, wherein the opaque housing consists of an upper cover and a lower base, and the display is disposed on the upper cover for observing, and the upper cover is detachably assembled to the lower base to define a receiving space which all around is opaque, to receive the loading platform, the light-emitting device, the magnetic field generator and the sensing device.

8. The device of claim 7, wherein the programable magnetron measurement unit further comprises a control interface disposed on the upper cover for adjusting a plurality of operating parameters, which at least include a strength of alternating magnetic field and a frequency of alternating magnetic field.

9. The device of claim 8, wherein the operating parameters further include a light intensity of the light-emitting device and a distance between the reaction container and the magnetic field generator.

10. The device of claim 8, wherein the magnetic field generator further comprises a control circuit and the electromagnet device having an excitation coil, and there are two electromagnet devices movably disposed on opposite two sides of the loading platform along the first direction respectively, and the control circuit is communicatively coupled to the processor and the two electromagnet devices, to receive a voltage signal from the processor and to control the current flowing through the excitation coil for changing the strength of alternating magnetic field.

11. The device of claim 9, wherein the operating parameters further include a plurality of conditions of the operating time, which at least comprises a duration of the operation time, a number of operation cycles, and an interval time of an operation cycle.

12. The device of claim 11, wherein the operating parameters further include an operating condition of each operation in the operation cycle, which at least comprises the strength of alternating magnetic field, the frequency of alternating magnetic field, the light intensity of the light-emitting device, and the distance between the reaction container and the magnetic field generator.

13. The device of claim 10, wherein the loading platform further includes a fixing frame and a slide rail kit connected with the fixing frame, the slide rail kit comprises a supporting rail and a loading body, and the loading body having a groove portion on its surface of one side for inserting the reaction container, and the loading body having a slideway portion on its surface of another side, which is being slidably and separably connected to the supporting rail along a second direction.

14. The device of claim 13, wherein the first direction and the second direction are non-parallel.

15. The device of claim 13, wherein the upper cover further includes a gate door disposed near to the loading platform, and the gate door is openable and closable, and the loading body can be taken into inside of the opaque housing and connected to the supporting rail along the second direction while the gate door is open.

16. The device of claim 1, wherein the reaction container is a cassette-type box which is made of glass or plastic, and the reaction container has a light-penetration area and the light-penetration area is at least 60% of the reaction container.

* * * * *